| United States Patent [19] | [11] Patent Number: 4,460,767 |
|---|---|
| Matsumura et al. | [45] Date of Patent: Jul. 17, 1984 |

[54] PROCESS FOR PRODUCTION OF SUGAR KETALS

[75] Inventors: Koichi Matsumura, Ibaraki; Tetsuya Aono, Nagaokakyo, both of Japan

[73] Assignee: Takeda Chemical Industries, Ltd., Osaka, Japan

[21] Appl. No.: 418,266

[22] Filed: Sep. 15, 1982

[30] Foreign Application Priority Data

Sep. 29, 1981 [JP] Japan ................................ 56-155071
Mar. 29, 1982 [JP] Japan ................................ 57-50575

[51] Int. Cl.$^3$ .......................... C07H 1/00; C07C 47/18
[52] U.S. Cl. .................................... 536/124; 536/18.5; 536/120; 568/594; 568/600
[58] Field of Search ...................... 536/120, 124, 18.5; 568/594, 600

[56] References Cited

U.S. PATENT DOCUMENTS

| 3,139,443 | 6/1964 | Sosnovsky | 568/594 |
| 3,598,804 | 8/1971 | Hindley et al. | 536/124 |
| 3,607,862 | 9/1971 | Jaffe et al. | 536/124 |
| 3,622,560 | 11/1971 | Hindley et al. | 536/124 |

*Primary Examiner*—Johnnie R. Brown
*Assistant Examiner*—Elli Peselev
*Attorney, Agent, or Firm*—Wegner & Bretschneider

[57] ABSTRACT

A process is disclosed for production of a sugar ketal, which comprises reacting a sugar with a ketone in the presence of (A) (1) copper, or an oxide, hydroxide or salt thereof and (2) hydrogen chloride or hydrogen bromide, or (B) cupric chloride or cupric bromide, said catalyst system being very effective in a small amount. The formation of unfavorable by-products can be reduced to a trace amount. The process offers the objective ketal in improved yields, and an industrially advantageous process.

10 Claims, No Drawings

PROCESS FOR PRODUCTION OF SUGAR KETALS

The present invention relates to a novel process for production of sugar ketals. More particularly, the present invention provides a process for producing sugar ketals in the presence of a catalyst. Production of sugar ketals is important for protection of hydroxyl groups of a sugar or for study of the structure of a sugar, and the sugar ketals are widely used as intermediates in various syntheses, for example, an intermediate for production of vitamin C, thus being very important from the industrial point of view.

The dehydration-condensation reaction of a sugar with a ketone is known as a ketal formation reaction, for which various methods have been proposed so far. The conventionally known methods involve the use of acid catalysts such as mineral acids exemplified by sulfuric acid, hydrogen chloride, hydrogen bromide, phosphoric acid and perchloric acid; organic acids exemplified by acetic acid, trifluoroacetic acid, methanesulfonic acid, p-toluenesulfonic acid and acidic ion exchange resins; or Lewis acids exemplified by anhydrous aluminum chloride, tin tetrachloride, boron trifluoride, anhydrous zinc chloride and ferric chloride. The ketal formation reaction is a dehydration-condensation reaction and, in almost all cases, the acid catalyst is used in large quantities so that the catalyst may serve as a dehydrating agent as well. In the event of a reduced amount of the acid catalyst it is necessary, furthermore, to use considerable quantities of dehydrating agents such as phosphorus pentoxide, calcium chloride, anhydrous sodium sulfate, anhydrous copper sulfate, pyrosulfates, metaphosphoric acid esters, alum and molecular sieves. That is to say, the conventional methods demand large quantities of acid catalysts and dehydrating agents. Therefore, the step of isolating the objective ketal from the reaction mixture is considerably troublesome. And a large amount of salts which are by-produced in the neutralization step and the used dehydrating agent are unfavorable industrial wastes. Thus, any one of the above conventional methods includes many problematic points as an industrial production process from the standpoints of post-treatment problems and saving of natural resources. In addition, these conventional methods entail a further disadvantage that side-reactions such as self-condensation of ketones are ready to take place, because the proposed catalysts are in every case strong acids. For example, U.S. Pat. No. 3,607,862 and 3,622,560 disclose the use of perchloric acid, ferric chloride and ferric bromide as a catalyst in the reaction of sugars and ketones. Though by use of these catalysts are much reduced production of unfavorable by-products such as a ketone dimer (e.g. acetone dimer) as compared with said conventional catalysts, these catalysts, however, still have a drawback of producing by-product to some extent.

The present inventors conducted an extensive investigation in order to eliminate such disadvantages as above, and have found that the reaction of a sugar with a ketone proceeds smoothly in the presence of copper or particular compounds thereof and hydrogen chloride or hydrogen bromide, and the process is able to produce a sugar ketal in good yields and to decrease the formation of by-products.

Furthermore, the present inventors have found that, in the above reaction use of specific copper compounds, i.e. cupric chloride or cupric bromide, brings about a good result in producing a sugar ketal even without adding hydrogen chloride or hydrogen bromide. Hitherto, in the sugar ketal formation reaction there has not been known use of copper or particular compounds thereof as a catalyst, though, in the reaction of $\alpha,\beta$-unsaturated aldehyde and monomeric alcohol use of metal salts has been studied.

Thus, the present invention is concerned with a process for producing a sugar ketal, which comprises reacting a sugar with a ketone in the presence of (A) (1) copper, or an oxide, hydroxide or salt thereof and (2) hydrogen chloride or hydrogen bromide, or (B) cupric chloride or cupric bromide.

The sugar usable in the present invention is not specifically limited, and is exemplified by a tetrose such as erythrose, threose and erythrulose, a pentose such as arabinose, xylose, ribose, lyxose, ribulose and xylulose, a hexose such as glucose, galactose, talose, idose, gulose, mannose, altrose, fructose, sorbose, tagatose and psicose, a deoxy-sugar such as rhamnose, fucose, 2-deoxyribose, and 2-deoxyglucose, and a sugar alcohol such as erythritol, ribitol, arabitol, mannitol, sorbitol, dulcitol and inositol. Among these sugars is valuable a pentose (e.g. arabinose and xylose) or a hexose (e.g. glucose, mannose, sorbose, galactose, fructose).

The ketone usable in the present invention is not specifically limited, and the preferred examples include an alkyl ketone such as acetone, methyl ethyl ketone, diethyl ketone, di-n-propyl ketone and di-i-propyl ketone, and a cyclic ketone such as cyclopentanone, cyclohexanone and cycloheptanone. Among these ketones is valuable acetone or cyclohexanone. The amount of these ketones to be used varies depending upon the structure of the objective compounds. The ketone is normally used in about 1 to 10 times the theoretical molar quantity; for example, it is preferable to use 1 mole or more of a ketone per mole of a sugar in the case of the objective compound being a monoketal, to use 2 moles or more of a ketone per mole of a sugar in the case of the objective compound being a diketal, and to use 3 moles or more of a ketone per mole of a sugar in the case of the objective compound being a triketal. Furthermore, the ketones may be used both as a reactant and a solvent, and in such case, a large excess of them may be used, unless they give any adverse effect on the reaction.

Copper usable in the process of the present invention includes copper powder. As examples of the copper oxide, there may be mentioned cuprous oxide and cupric oxide; as examples of the copper hydroxide, there may be mentioned cuprous hydroxide, cupric hydroxide, etc.; and examples of the copper salt include (a) copper halides (e.g., cuprous halides exemplified by cuprous chloride, cuprous bromide, cuprous iodide, etc., cupric halides exemplified by cupric chloride, cupric bromide, cupric fluoride, etc., and the like), (b) salts of copper with inorganic acids (e.g., cuprous sulfide, cuprous cyanide, cuprous thiocyanate, cupric sulfide, cupric fluoborate, cupric fluosilicate, cupric arsenite, cupric perchlorate, cupric sulfate, cupric phosphate, cupric pyrophosphate, cupric cyanide, cupric thiocyanate, etc.), and (c) salts of copper with organic acids (e.g., cupric formate, cupric acetate, cupric oxalate, cupric citrate, cupric benzoate, cupric oleate, cupric stearate, cupric acetylacetonate, etc.). Among these copper and copper compounds is preferable copper oxide, copper hydroxide or copper salt.

The above-mentioned salts of copper may be either in the form of an anhydride or a hydrate.

Copper, or its oxides, hydroxides or salts used in the present invention may be one kind of the compound or a mixture of two or more kinds of the compounds.

The hydrogen chloride or hydrogen bromide may be added to the reaction mixture as it is or in the form of its solution. The solvent may be water or an organic solvent (e.g., diethyl ether, dioxane, nitromethane, dichloromethane, chloroform, carbon tetrachloride, benzene, toluene, xylene, etc.).

In reference to the amount of the above-mentioned copper, or an oxide, hydroxide or salt thereof to be used, they can be employed in an amount of not less than 0.01 weight %, preferably within the range of about 0.03 weight % to about 10 weight %, based on the weight of a sugar, and further preferably in amounts within the range of about 0.1 weight % to about 7 weight % against the sugar used. Cupric chloride and cupric bromide catalysts can be used in the same amount.

The amount of hydrogen chloride or hydrogen bromide to be used is about 0.1 to about 5 moles per mole of copper, or its oxide, its hydroxide or its salt, preferably in the range of about 0.2 to about 4 moles. In employing cupric chloride or cupric bromide as a catalyst, use of hydrogen chloride or hydrogen bromide is not always essential.

The reaction may be carried out in a solvent. As the reaction solvent, use can be made of any solvent which does not participate in the reaction, and there may be mentioned, for example, ether, tetrahydrofuran, dimethoxyethane, dioxane, acetonitrile, propionitrile, nitromethane, dichloromethane, chloroform, carbon tetrachloride, 1,1-dichloroethane, 1,2-dichloroethane, methyl acetate, ethyl acetate, pentane, cyclopentane, hexane, cyclohexane, heptane, benzene, toluene, xylene, etc. In addition, the above-mentioned ketones can also be used as a solvent, and the reaction can be conducted in a solvent mixture of two or more kinds of said solvents. Further, a small amount of water may be added in order to enhance the solubilities of the sugars and catalysts to said solvent.

The reaction is an equilibrium reaction, and it is, therefore, recommandable that the reaction may be conducted while continuously removing the water produced in the reaction system. Complete removal of the water results in good yields of the ketals. As the method for removing the water from the reaction system, the conventional manners can be used. There may be mentioned, for example, distillation, use of a drying agent and so on. In the case of the removal by distillation, the manner of utilizing an azeotrope between a solvent and water is commonly used. In this manner, after separating water from the liquid obtained by cooling azeotropically distilled vapor, the recovered solvent may be returned to the reaction vessel; or after removing the distilled vapor from the reaction vessel, the same amount of new dry solvent may be added to the reaction vessel. As the manner of using drying agents, the vapor directly, or the liquid obtained by cooling the vapor, may be dried with drying agents represented by anhydrous calcium sulfate, molecular sieves and alumina and then the dried solvent may be returned to the reaction vessel.

The reaction is carried out usually at temperatures within the range of about 0° C. to 150° C., but the reaction temperature is preferably in the range of about 20° C. to 100° C. Further, the reaction may be conducted under reduced pressure in order to control a boiling point of an azeotrope between a solvent or a ketone and water.

The reaction time varies with the types of sugars and ketones, amount of the catalyst and other reaction conditions, and is normally in the region of about 30 minutes to 10 hours, preferably in the range of about 1 hour to 5 hours.

In order to isolate the sugar ketal thus obtained from the reaction mixture, the reaction solvent is distilled off. This distillation may be carried out after a small amount of alkalis (e.g., sodium hydrogencarbonate, potassium hydrogencarbonate, sodium carbonate, potassium carbonate, sodium hydroxide, potassium hydroxide, ammonia etc.) or aqueous solutions of said alkalis are added to adjust the pH of the reaction mixture to a weak alkalinity (a pH of about 7 to 9). From the resultant residue, the objective sugar ketal can be readily obtained by the known separating manners such as extraction, distillation, column chromatography or recrystallization.

The present invention provides an industrially advantageous process for producing sugar ketals.

The catalyst system of the present invention is very effective even in a small amount. The amount of the catalyst to be used in the process may be decreased accordingly. Particularly, though cupric chloride catalyst and cupric bromide catalyst are nearly neutral salts, these catalysts are very active even in a small amount as a catalyst for ketal formation reaction with or without hydrogen chloride or hydrogen bromide.

The process of the present invention does not demand troublesome post-treatments for purification. The formation of unfavorable by-products such as a ketone dimer can be reduced to a trace amount. The process offers the objective ketal in improved yields.

According to the process of the present invention, furthermore, the reaction time can be shortened, the amount of a solvent to be used can be reduced, and the quantities of energy to be supplied to the reaction system can be lessened. The catalyst (copper or its oxide, its hydroxide or its salt) can be easily recovered and recycled.

Moreover, according to the process of the present invention, there do not afford industrial wastes such as ammonium sulfate which are formed in the conventional methods.

The examples are described below to illustrate the present invention more specifically.

EXAMPLE 1

To 200 ml of acetone were added 10.0 g of D-xylose, 138 mg of cupric fluoride dihydrate and 1 ml of a 2 mole/l solution of hydrogen chloride in dioxane, and the mixture was stirred for 7 hours under reflux on a warm-water bath at 60° C. The refluxing solvent was continuously dried with 20 g of molecular sieves 3A (produced by Wako Pure Chemical Ind., Ltd.) which was placed between the reaction vessel and the cooling tube. After the conclusion of the reaction, a small amount of aqueous sodium hydrogencarbonate was added to the reaction mixture and the acetone was distilled off under reduced pressure. The residue was dissolved in benzene, and the solution was washed with aqueous sodium hydrogencarbonate and water, and dried over anhydrous magnesium sulfate. When the benzene was distilled off under reduced pressure, there was obtained 12.8 g (83.7%) of 1,2:3,5-di-O-isopropylidene-α-D-xylofuranose as a residue in the form of an oily material (purity of not less than 97%). The compound showed a boiling point of 94° to 97° C./3 mmHg.

EXAMPLE 2

To a mixed solution of 150 ml of dimethoxyethane and 50 ml of cyclohexanone were added 10.0 g of D-glucose, 150 mg of cupric hydroxide and 1 ml of a 2 mole/l solution of hydrogen chloride in dioxane, and the mixture was stirred for 7 hours under reflux in an oil bath at 95° C. The refluxing solvent was continuously dried with 20 g of molecular sieve 3A which was placed between the reaction vessel and the cooling tube. After the conclusion of the reaction, the reaction solution was diluted with benzene, washed with aqueous sodium hydrogencarbonate and water, and dried over anhydrous magnesium sulfate. When the solvent and cyclohexanone were distilled off under reduced pressure, there was obtained 15.5 g (82.1%) of 1,2:5,6-di-O-cyclohexylidene-α-D-glucofuranose as a residue. The compound, when recrystallized from ligroin, showed a melting point of 133° to 135° C.

Elemental analysis, for $C_{18}H_{28}O_6$; Calcd.: C, 63.51; H, 8.29; Found: C, 63.75; H, 8.20.

EXAMPLE 3

To a mixed solution of 150 ml of cyclohexanone and 120 ml of dichloromethane were added 10.0 g of D-mannose, 200 mg of cupric acetate monohydrate and 1 ml of a 2 mole/l solution of hydrogen chloride in dioxane, and the mixture was stirred for 7 hours under reflux in a warm-water bath at 65° C. The refluxing solvent was continuously dried with 20 g of molecular sieves 3A which was placed between the reaction vessel and the cooling tube. After the conclusion of the reaction, the reaction solution was diluted with benzene, washed with aqueous sodium hydrogen-carbonate and water, and dried over anhydrous magnesium sulfate. When the solvent and cyclohexanone were distilled off under reduced pressure, there was obtained 17.5 g (92.6%) of 2,3:5,6-di-O-cyclohexylidene-α-D-mannofuranose as a residue. The compound, when recrystallized from hexane, showed a melting point of 122° to 124° C.

Elemental analysis, for $C_{18}H_{28}O_6$; Calcd.: C, 63.51; H, 8.29; Found: C, 63.47; H, 8.29.

EXAMPLE 4

To 200 ml of acetone were added 10.0 g of D-fructose, 99 mg of cuprous chloride and 1 ml of a 2 mole/l of hydrogen chloride in dioxane, and the mixture was stirred for 5 hours under reflux in a warm-water bath at 60° C. The refluxing solvent was continuously dried with 20 g of molecular sieves 3A which was placed between the reaction vessel and the cooling tube. After the conclusion of the reaction, a small amount of aqueous sodium hydrogencarbonate was added to the reaction solution, and the acetone was distilled off under reduced pressure. The residue was dissolved in benzene, and the solution was washed with aqueous sodium hydrogencarbonate and water, and dried over anhydrous magnesium sulfate. When the benzene was distilled off under reduced pressure, there was obtained 10.0 g (68.2%) of 2,3:4,5-di-O-isopropylidene-β-D-fructopyranose. The compound, when recrystallized from n-hexane, showed a melting point of 96° to 98° C.

Elemental analysis, for $C_{12}H_{20}O_6$; Calcd.: C, 55.37; H, 7.75; Found: C, 55.41; H, 7.78.

EXAMPLE 5

To 200 ml of acetone were added 10.0 g of L-sorbose, 200 mg of cupric acetate monohydrate and 1 ml of a 2 mole/l solution of hydrogen chloride in dioxane, and the mixture was stirred for 7 hours under reflux in a warm-water bath at 60° C. The refluxing solvent was continuously dried with 20 g of molecular sieves 3A which was placed between the reaction vessel and the cooling tube. After the conclusion of the reaction, a small amount of aqueous sodium hydrogencarbonate was added to the reaction mixture, and the acetone was distilled off under reduced pressure. The residue was dissolved in benzene, and the solution was washed with aqueous sodium hydrogencarbonate and water, and dried over anhydrous magnesium sulfate. When the benzene was distilled off under reduced pressure, there was obtained 11.4 g (78.9%) of 2,3:4,6-di-O-isopropylidene-L-sorbofuranose as a residue. The compound, when recrystallized from petroleum ether, showed a melting point of 77° to 78° C.

Elemental analysis, for $C_{12}H_{20}O_6$; Calcd.: C, 55.37; H, 7.75; Found: C, 55.48; H, 7.81.

EXAMPLE 6

To 200 ml of acetone were added 10.0 g of L-sorbose, 99 mg of cuprous chloride and 1 ml of a 2 mole/l solution of hydrogen chloride in dioxane, and the mixture was stirred for 4 hours under reflux in a warm-water bath at 60° C. The refluxing solvent was continuously dried with 20 g of molecular sieves 3A which was placed between the reaction vessel and the cooling tube. After the conclusion of the reaction, the same post-treatment as in Example 5 was carried out, thus giving 10.99 g (76.1%) of 2,3:4,6-di-O-isopropylidene-L-sorbofuranose.

EXAMPLE 7

To 200 ml of acetone were added 10.0 g of L-sorbose, 143 mg of cuprous oxide and 173 mg of 47% hydrobromic acid, and the mixture was refluxed in a warm-water bath at 60° C. for 8 hours. The refluxing solvent was continuously dried with 20 g of molecular sieves 3A which was placed between the reaction vessel and the cooling tube. After the conclusion of the reaction, the same post-treatment as in Example 5 was carried out, thus giving 11.0 g (76.2%) of 2,3:4,6-di-O-isopropylidene-L-sorbofuranose.

EXAMPLE 8

To 200 ml of acetone were added 10.0 g of D-mannitol, 200 mg of cupric acetate monohydrate and 1 ml of a 2 mole/l solution of hydrogen chloride in dioxane, and the mixture was stirred for 7 hours under reflux in a warm-water bath at 60° C. The refluxing solvent was continuously dried with 20 g of molecular sieves 3A which was placed between the reaction vessel and the cooling tube. After the conclusion of the reaction, a small amount of aqueous sodium hydrogencarbonate was added to the reaction mixture, and the acetone was distilled off under reduced pressure. The residue was dissolved in chloroform, and the solution was washed with aqueous sodium hydrogencarbonate and water, and dried over anhydrous magnesium sulfate. When the chloroform was distilled off under reduced pressure, there was obtained 16.2 g (97.7%) of 1,2:3,4,:5,6-tri-O-isopropylidene-D-mannitol (purity of 88%) as a residue.

The compound, when recrystallized from 70% aqueous ethanol, showed a melting point of 68° to 70° C.

Elemental analysis, for $C_{15}H_{26}O_6$; Calcd.: C, 59.58; H, 8.67; Found: C, 59.64; H, 8.63.

EXAMPLE 9

To a mixed solution of 150 ml of cyclohexanone and 120 ml of dichloromethane were added 10.0 g of D-arabinose, 196 mg of cupric hydroxide and 1 ml of a 2 mole/l solution of hydrogen chloride, and the mixture was stirred for 7 hours under reflux in a warm-water bath at 65° C. The refluxing solvent was continuously dried with 20 g of molecular sieves 3A which was placed between the reaction vessel and the cooling tube. After the conclusion of the reaction, the reaction solution was diluted with benzene, washed with aqueous sodium hydrogencarbonate and water, and dried over anhydrous magnesium sulfate. When the solvent and cyclohexanone were distilled off under reduced pressure, there was obtained 17.93 g (98.3%) of di-O-cyclohexylidene-D-arabinose (purity of not less than 99%) as a residue. m.p. 73.5°–75.5° C. (recrystallized from petroleum ether).

Elemental analysis, for $C_{17}H_{26}O_5$; Calcd.: C, 65.78; H, 8.44; Found: C, 65.70; H, 8.40.

EXAMPLE 10

By the same procedure as in Example 5, there was obtained 2,3:4,6-di-O-isopropylidene-L-sorbofuranose from L-sorbose. Shown in the following table is the yield of the objective compound versus the type of reactants, used amount thereof and reaction time.

Elemental analysis, for $C_{17}H_{26}O_5$; Calcd.: C, 65.78; H, 8.44; Found: C, 65.54; H, 8.49.

EXAMPLE 12

To 250 ml of acetone were added 10.0 g of D-xylose and 125 mg of anhydrous cupric chloride, and the mixture was stirred for 8.5 hours under reflux in a warm-water bath at 60° C. The refluxing solvent was continuously dried with 20 g of molecular sieves 3A which was placed between the reaction vessel and the cooling tube. After the conclusion of the reaction, a small amount of aqueous sodium hydrogencarbonate was added to the reaction mixture and the acetone was distilled off under reduced pressure. The residue was dissolved in benzene, and the benzene solution was washed with aqueous sodium hydrogencarbonate and water, and dried over anhydrous magnesium sulfate. When the benzene was distilled off under reduced pressure, there was obtained 13.9 g (91%) of 1,2:3,5-di-O-isopropylidene-α-D-xylofranose (purity of not less than 98.7%) as an oily material. The compound showed a boiling point of 93° to 97° C./3 mmHg.

EXAMPLE 13

To a mixed solution of 150 ml of cyclohexanone and 120 ml of dichloromethane were added 10.0 g of D-xylose and 125 mg of anhydrous cupric chloride, and the mixture was stirred for 8.5 hours under reflux in a warm-water bath at 65° C. The refluxing solvent was continuously with 20 g of molecular sieves 3A which was placed between the reaction vessel and the cooling tube. The reaction solution was diluted with benzene,

| Amount of L-sorbose, g. | Type and amount of copper, its oxide, hydroxide or salt, mg. | Amount of hydrogen chloride, mmol. | Reaction time, hr. | Yield of 2,3:4,6-di O—isopropylidene-L-sorbofuranose, % |
| --- | --- | --- | --- | --- |
| 10.0 | Cupric chloride dihydrate, 170 | 2 | 3 | 57.9 |
| 10.0 | Cuprous chloride, 99 | 2 | 3 | 58.0 |
| 10.0 | Cuprous bromide, 143 | 2 | 3 | 55.6 |
| 10.0 | Cupric fluoride dihydrate, 138 | 2 | 3 | 63.1 |
| 10.0 | Cupric sulfate pentahydrate, 250 | 2 | 3 | 58.0 |
| 10.0 | Cupric pyrophosphate trihydrate, 355 | 2 | 3 | 64.2 |
| 10.0 | Cupric formate tetrahydrate, 225 | 2 | 3 | 59.9 |
| 10.0 | Cuprous cyanide, 90 | 2 | 3 | 53.0 |
| 10.0 | Cuprous oxide 143 | 2 | 3 | 56.2 |
| 10.0 | Cupric oxide, 200 | 2 | 3 | 65.6 |
| 10.0 | Cupric hydroxide, 98 | 4 | 3 | 58.4 |
| 10.0 | Copper powder, 64 | 2 | 3 | 37.6 |

EXAMPLE 11

To a mixed solution of 150 ml of cyclohexanone and 120 ml of dichloromethane were added 10.0 g of D-arabinose and 125 mg of anhydrous cupric chloride, and the mixture was stirred for 9 hours under reflux on a warm-water bath at 63° to 65° C. The refluxing solvent was continuously dried with 20 g of molecular sieves 3A (produced by Wako Pure Chemical Ind., Ltd.) which was placed between the reaction vessel and the cooling tube. The reaction solution was diluted with benzene, washed with aqueous sodium hydrogencarbonate and water, and dried over anhydrous magnesium sulfate. When the solvent and cyclohexanone were distilled off under reduced pressure, there was obtained 19.4 g (94%) of di-O-cyclohexylidene-D-arabinose (purity of not less than 98%) as a residue. After recrystallization from petroleum ether, the compound showed a melting point of 73.5° to 75.5° C.

washed with aqueous sodium hydrogencarbonate and water, and dried over anhydrous magnesium sulfate. When the solvent and cyclohexanone were distilled off under reduced pressure, there was obtained 20.0 g (97%) of 1,2:3,5-di-O-cyclohexylidene-α-D-xylofuranose (purity of not less than 95%) as a residue. The compound, when recrystallized from petroleum ether, showed a melting point of 104.5° to 105.5° C.

Elemental analysis, for $C_{17}H_{26}O_5$; Calcd.: C, 65.78; H, 8.44; Found: C, 65.91; H, 8.45.

EXAMPLE 14

To 500 ml of acetone were added 20.0 g of D-ribose and 250 mg of anhydrous cupric chloride, and the mixture was stirred for 5 hours under reflux in a warm-water bath at 58° C. The refluxing solvent was continuously dried with 30 g of molecular sieves 3A which was placed between the reaction vessel and the cooling tube. After the conclusion of the reaction, a small amount of aqueous sodium hydrogencarbonate is added to the reaction mixture, and the acetone was distilled off under reduced pressure. The residue was dissolved in benzene, and the solution was washed with aqueous sodium hydrogencarbonate and water, and dried over anhydrous magnesium sulfate. The benzene was distilled off under reduced pressure and the residue was subjected to distillation under reduced pressure, producing 13 g (51%) of 2,3-O-isopropylidene-D-ribofuranose as a fraction of 109°–112° C./0.04 mmHg.

Elemental analysis, for $C_8H_{14}O_5$; Calcd.: C, 50.52; H, 7.42; Found: C, 50.41; H, 7.47.

EXAMPLE 15

To 250 ml of acetone were added 10.0 g of D-glucose and 125 mg of anhydrous cupric chloride, and the mixture was stirred for 9 hours under reflux in a warm-water bath at 57° to 58° C. The refluxing solvent was continuously dried with 20 g of molecular sieves 3A which was placed between the reaction vessel and the cooling tube. After the conclusion of the reaction, a small amount of aqueous sodium hydrogencarbonate was added to the reaction mixture, and the acetone was distilled off under reduced pressure. The residue was dissolved in benzene, and the benzene solution was washed with aqueous sodium hydrogencarbonate and water, and dried over anhydrous magnesium sulfate. When the benzene was distilled off under reduced pressure, there was obtained 12.4 g (86%) of 1,2:5,6-di-O-isopropylidene-α-D-glucofuranose (purity of not less than 97%). The compound, when recrystallized from a solvent mixture of chloroform-hexane (1:2), showed a melting point of 107° to 109° C.

Elemental analysis, for $C_{12}H_{20}O_6$; Calcd.: C, 55.37; H, 7.75; Found: C, 55.64; H, 7.64.

EXAMPLE 16

To a mixed solution of 150 ml of cyclohexanone and 120 ml of dichloromethane were added 10.0 g of D-glucose and 125 mg of anhydrous cupric chloride, and the mixture was stirred for 8.5 hours under reflux in a warm-water bath at 63° C. The refluxing solvent was continuously dried with 20 g of molecular sieves 3A which was placed between the reaction vessel and the cooling tube. The reaction solution was diluted with chloroform, washed with aqueous sodium hydrogencarbonate and water, and dried over anhydrous magnesium sulfate. The solvent and cyclohexanone were distilled off under reduced pressure, and the residue was recrystallized from ligroin, thus affording 9.6 g (51%) of 1,2:5,6-di-O-cyclohexylidene-α-D-glucofuranose. m.p. 133°–136° C.

Elemental analysis, for $C_{18}H_{28}O_6$; Calcd.: C, 63.51; H, 8.29; Found: C, 63.75; H, 8.20.

EXAMPLE 17

To 250 ml of acetone were added 10.0 g of D-galactose and 125 mg of anhydrous cupric chloride, and the mixture was stirred for 8 hours under reflux in a warm-water bath at 57° to 58° C. The refluxing solution was continuously dried with 20 g of molecular sieves 3A which was placed between the reaction vessel and the cooling tube. After the conclusion of the reaction, a small amount of aqueous sodium hydrogencarbonate is added to the reaction mixture and the acetone was distilled off under reduced pressure. The residue was dissolved in benzene, and the solution was washed with aqueous sodium hydrogencarbonate and water, and dried over anhydrous magnesium sulfate. The residue obtained by distilling off the benzene was subjected to distillation under reduced pressure, thus producing 7.9 g (55%) of 1,2:3,4-di-O-isopropylidene-α-D-galactopyranose as a fraction of 130° to 133° C./0.2 mmHg.

Elemental analysis, for $C_{12}H_{20}O_6$; Calcd.: C, 55.37; H, 7.75; Found: C, 55.48; H, 7.78.

EXAMPLE 18

To 250 ml of acetone were added 10.0 g of D-mannose and 125 mg of anhydrous cupric chloride, and the mixture was stirred for 3 hours under reflux in a warm-water bath at 57° to 58° C. The refluxing solvent was continuously dried with 20 g of molecular sieves 3A which was placed between the reaction vessel and the cooling tube. After the conclusion of the reaction, a small amount of aqueous sodium hydrogencarbonate was added to the reaction mixture, and the acetone was distilled off under reduced pressure. The residue was dissolved in benzene, and the benzene solution was washed with aqueous sodium hydrogencarbonate and water, and dried over anhydrous magnesium sulfate. When the benzene was distilled off under reduced pressure, there was obtained 13.0 g (90%) of 2,3:5,6-di-O-isopropylidene-α-D-mannofuranose (purity of not less than 92%). The compound, when recrystallized from petroleum ether, showed a melting point of 122° to 123° C.

Elemental analysis, for $C_{12}H_{20}O_6$; Calcd.: C, 55.37; H, 7.75; Found: C, 55.64; H, 7.78.

EXAMPLE 19

To a mixed solution of 150 ml of cyclohexanone and 120 ml of dichloromethane were added 10.0 g of D-mannose and 125 mg of anhydrous cupric chloride, and the mixture was stirred for 9 hours under reflux in a warm-water bath at 63° to 65° C. The refluxing solvent was continuously dried with 20 g of molecular sieves 3A which was placed between the reaction vessel and cooling tube. The reaction solution was diluted with benzene, washed with aqueous sodium hydrogencarbonate and water, and dried over anhydrous magnesium sulfate. When the solvent and cyclohexanone were distilled off under reduced pressure, there was obtained 17.9 g (95%) of 2,3:5,6-di-O-cyclohexylidene-α-D-mannofuranose (purity of not less than 95%) as a residue. The compound, when recrystallized from n-hexane, showed a melting point of 122° to 124° C.

Elemental analysis, for $C_{18}H_{28}O_6$; Calcd.: C, 63.51; H, 8.29; Found: C, 63.47; H, 8.24.

EXAMPLE 20

To 250 ml of acetone were added 10.0 g of D-fructose and 125 mg of anhydrous cupric chloride, and the mixture was stirred for 6 hours under reflux in a warm-water bath at 57° to 58° C. The refluxing solvent was continuously dried with 20 g of molecular sieves 3A which was placed between the reaction vessel and the cooling tube. After the conclusion of the reaction, a small amount of aqueous sodium hydrogencarbonate is added to the reaction mixture, and the acetone was distilled off under reduced pressure. The residue was dissolved in benzene, and the benzene solution was washed with aqueous sodium hydrogencarbonate and water, and dried over anhydrous magnesium sulfate. When the benzene was distilled off under reduced pressure, there was obtained 12.2 g of 2,3:4,5-di-O-isopropylidene-β-D-fructopyranose (85%). The compound, when recrystallized from n-hexane showed a melting point of 96° to 98° C.

Elemental analysis, for $C_{12}H_{20}O_6$; Calcd.: C, 55.37; H, 7.75; Found: C, 55.64; H, 7.44.

EXAMPLE 21

To 250 ml of acetone were added 10.0 g of L-sorbose and 125 mg of anhydrous cupric chloride, and the mixture was stirred for 4 hours under reflux in a warm-water bath at 57° to 58° C. The refluxing solvent was continuously dried with 14 g of molecular sieves 3A which was placed between the reaction vessel and the cooling tube. After cooling, a small amount of aqueous sodium hydrogencarbonate is added to the reaction mixture, and the acetone was distilled off under reduced pressure. The residue was dissolved in about 150 ml of benzene and the benzene solution was washed with aqueous sodium hydrogencarbonate and water, and dried over anhydrous magnesium sulfate. When the benzene was distilled off under reduced pressure, there was obtained 12.1 g (84%) of 2,3:4,6-di-O-isopropylidene-L-sorbofuranose (purity of not less than 98%) as a residue. Its infra-red absorption spectrum and nuclear magnetic resonance spectrum were in accordance with those of the crystals as obtained in Example 5.

EXAMPLE 22

To 500 ml of acetone were added 20 g of L-sorbose and 250 mg of anhydrous cupric bromide, and the mixture was stirred for 7 hours under reflux in a warm-water bath at 57° to 58° C. The refluxing solvent was continuously dried with 30 g of molecular sieves 3A which was placed between the reaction vessel and the cooling tube. After cooling, a small amount of aqueous sodium hydrogencarbonate is added to the reaction mixture, and the acetone was distilled off under reduced pressure. The residue was dissolved in 300 ml of benzene, and the benzene solution was washed with aqueous sodium hydrogencarbonate and water, and dried over anhydrous magnesium sulfate. When the benzene was distilled off under reduced pressure, there was obtained 23.0 g (80%) of 2,3:4,6-di-O-isopropylidene-L-sorbofuranose (purity of not less than 98%) as a residue. The compound, when recrystallized from petroleum ether, showed a melting point of 77° to 78° C., and exhibited the same infrared absorption spectrum and nuclear magnetic resonance spectrum as those of the crystals as obtained in Example 5.

EXAMPLE 23

In a three-necked flask of 300 ml capacity fitted with a device for distillation were placed 10.0 g of L-sorbose, 100 mg of anhydrous cupric bromide and 250 ml of acetone, and the mixture was stirred for 5 hours under reflux in a warm-water bath at 60° C. The acetone containing the water produced in the reaction was continuously distilled off from the reaction mixture and acetone was continuously fed to maintain the reaction solution in the flask at 250 ml. The resultant reaction solution was subjected to the same post-treatment as in Example 21, thus producing 12.0 g (83%) of 2,3:4,6-di-O-isopropylidene-L-sorbofuranose.

EXAMPLE 24

To a mixed solution of 150 ml of cyclopentanone and 120 ml of dichloromethane were added 10.0 g of L-sorbose and 125 mg of anhydrous cupric chloride, and the mixture was stirred for 8 hours under reflux in a warm-water bath at 65° C. The refluxing solvent was continuously dried with 20 g of molecular sieves 3A which was placed between the reaction vessel and the cooling tube. After the conclusion of the reaction, the unreacted L-sorbose (4.3 g) was filtered out, and the reaction solution was diluted with benzene, washed with aqueous sodium hydrogencarbonate and water, and dried over anhydrous magnesium sulfate. The solvent and cyclopentanone were distilled off under reduced pressure, and the residue was recrystallized from hexane, thus producing 5.3 g (53.8% on the basis of the consumed L-sorbose) of 2,3:4,6-di-O-cyclopentylidene-α-L-sorbofuranose, m.p. 136°–138° C.

Elemental analysis, for $C_{16}H_{24}O_6$; Calcd.: C, 61.52; H, 7.75; Found: C, 61.42; H, 7.73.

EXAMPLE 25

To 150 ml of dimethoxyethane were added 10.0 g of L-sorbose, 50 ml of cyclohexanone and 125 mg of anhydrous cupric chloride, and the mixture was stirred for 8 hours under reflux in a warm-water bath at 84° C. The refluxing solvent was continuously dried with 20 g of molecular sieves 3A which was placed between the reaction vessel and the cooling tube. The reaction solution was diluted with benzene, washed with aqueous sodium hydrogencarbonate and water, and dried over anhydrous magnesium sulfate. When the solvent and cyclohexanone were distilled off under reduced pressure, there was obtained 13.4 g (71%) of 2,3:4,6-di-O-cyclohexylidene-L-sorbofuranose (purity of not less than 91%). The compound, when recrystallized from petroleum ether, showed a melting point of 118° to 119° C.

Elemental analysis, for $C_{18}H_{28}O_6$; Calcd.: C, 63.51; H, 8.29; Found: C, 63.39; H, 8.31.

EXAMPLE 26

To 250 ml of acetone were added 10.0 g of D-mannitol and 125 mg of anhydrous cupric chloride, and the mixture was stirred for 8 hours under reflux in a warm-water bath at 58° C. The refluxing solvent was continuously dried with 20 g of molecular sieves 3A which was placed between the reaction vessel and the cooling tube. After the conclusion of the reaction, the acetone was distilled off under reduced pressure, and the residue was dissolved in chloroform. The chloroform solution was washed with aqueous sodium hydrogencarbonate and water, and dried over anhydrous magnesium sulfate. When the chloroform was distilled under reduced pressure, there was obtained 16.0 g (96.4%) of 1,2:3,4:5,6-tri-O-isopropylidene-D-mannitol (purity of not less than 92%). The compound, when recrystallized from 70% ethanol, showed a melting point of 68.5° to 70.5° C.

Elemental analysis, for $C_{15}H_{26}O_6$; Calcd.: C, 59.58; H, 8.67; Found: C, 59.67; H, 8.22.

EXAMPLE 27

To a mixed solution of 150 ml of cyclohexanone and 120 ml of dichloromethane were added 10 g of dulcitol and 125 mg of anhydrous cupric chloride, and the mixture was stirred for 8 hours under reflux in a warm-water bath at 65° C. The refluxing solvent was continuously dried with 20 g of molecular sieves 3A which was placed between the reaction vessel and the cooling tube. The reaction solution was diluted with benzene, then washed with aqueous sodium hydrogencarbonate and water, and dried over anhydrous magnesium sulfate. The solvent and cyclohexanone were distilled off under reduced pressure, and the residue was recrystallized from ethanol, thus producing 6.6 g (35%) of di-O-cyclohexylidenedulcitol. m.p. 145°–149° C.

Elemental analysis, for $C_{18}H_{30}O_6$; Calcd.: C, 63.13; H, 8.83; Found: C, 63.17; H, 8.94.

What is claimed is:

1. A process for producing a sugar ketal which comprises reacting a sugar of the class consisting of erythrose, threose, erythrulose, arabinose, xylose, ribose, lyxose, ribulose, xylulose, glucose, galactose, talose, idose, gulose, mannose, altrose, fructose, sorbose, tagatose, and psicose, rhamnose, fucose, 2-deoxyribose, and 2-deoxyglucose, erythritol, ribitol, arabitol, mannitol, sorbitol, dulcitol, and inositol with a ketone of the class consisting of the di-($C^{1-3}$-lower alkyl) ketones and $C^{5-7}$-cycloalkanones in the presence of a catalyst which is a member of the class consisting of copper, an oxide, hydroxide or salt thereof when used in presence of hydrogen chloride or hydrogen bromide or a catalyst which is a member of the class consisting cupric chloride and cupric bromide.

2. A process according to claim 1, wherein the sugar is a pentose or a hexose.

3. A process according to claim 2, wherein the hexose is sorbose.

4. A process according to claim 1, wherein the ketone is acetone.

5. A process according to claim 1, wherein the reaction is carried out in the presence of (1) copper, or an oxide, hydroxide or salt thereof and (2) hydrogen chloride or hydrogen bromide.

6. A process according to claim 1, wherein the reaction is carried out in the presence of cupric chloride or cupric bromide.

7. A process according to claim 1, wherein the amount of copper, or an oxide, hydroxide or salt thereof is not less than 0.01 weight % based on the weight of a sugar and the amount of hydrogen chloride or hydrogen bromide is about 0.1 to 5 moles per mole of copper, or an oxide, hydroxide or salt thereof.

8. A process according to claim 1, wherein the reaction is carried out at temperatures within the range of about 0° C. to 150° C.

9. A process according to claim 1, wherein the reaction is carried out while continuously removing water from the reaction system.

10. A process according to claim 1, wherein the amount of cupric chloride or cupric bromide is not less than 0.01 weight percent based on the weight of the sugar.

* * * * *